United States Patent
Johnson et al.

(10) Patent No.: US 6,355,822 B1
(45) Date of Patent: Mar. 12, 2002

(54) PROCESS FOR SELECTIVE REDUCTION

(75) Inventors: Dean Vincent Johnson, Graz; Peter Pöchlauer, Linz; Herfried Griengl, Graz, all of (AT)

(73) Assignee: DSM Fine Chemicals Austria Nfg GmbH & CoKG, Linz (AT)

(*) Notice: Subject to any disclaimer, the term of this patent is extended or adjusted under 35 U.S.C. 154(b) by 0 days.

(21) Appl. No.: 09/616,875

(22) Filed: Jul. 14, 2000

(30) Foreign Application Priority Data

Jul. 16, 1999 (AU) .............................................. 1236/99

(51) Int. Cl.$^7$ .................................................. C07F 7/08
(52) U.S. Cl. ........................... 556/442; 552/4; 549/214; 554/77
(58) Field of Search ............................. 556/442; 552/4; 549/214; 554/77

(56) References Cited

U.S. PATENT DOCUMENTS 5,442,105 A * 8/1995 Sayo et al. .................. 552/4 X

FOREIGN PATENT DOCUMENTS

EP 0 320 096 6/1989

OTHER PUBLICATIONS

F.D. Polyak et al., "Asymmetric Reduction of Acetoacetic Ester by Chirally Modified Sodium Borohydride", Synthetic Communications, 21 (10&11), 1137–1142 (1991).

* cited by examiner

Primary Examiner—Paul F. Shaver
(74) Attorney, Agent, or Firm—Wenderoth, Lind & Ponack, LLP

(57) ABSTRACT

Process for the stereoselective reduction of chiral α- or β-keto esters which have a chiral center in the γ position in an inert solvent at temperatures from −80 to +50° C. using a reductant obtained by reaction of $NaBH_4$ and (D)- or (L)-tartaric acid, to give the corresponding diastereomeric hydroxy compounds in each case.

9 Claims, No Drawings

PROCESS FOR SELECTIVE REDUCTION

Chirally functionalized alcohols are very important synthetic intermediates, for example for potential enzyme inhibitors for anticancer therapy, such as, for example, protein kinase C inhibitors, or for anti-HIV agents.

For this reason, many experiments have already been undertaken to obtain these compounds from prochiral ketones.

One of the most customary methods for the preparation of optically active α-hydroxy esters is the asymmetric reduction of the corresponding α-keto esters. Thus the asymmetric reduction of prochiral ketones with chiral systems derived from $NaBH_4$, which are obtained by reaction $NaBH_4$ with, for example, monosaccharides or α-amino acid derivatives, in particular L-proline derivatives, has already been more closely investigated. However, this method only produces moderate optical purities, as is known from Bull. Chem. Soc. Jpn., 64, 175–182 (1991). For this reason, other chiral systems derived from $NaBH_4$ were investigated in this reference. Thus ethyl 2-(3,4-isopropylidenedioxyphenyl)-2-oxoacetate was reduced to the corresponding (R)-hydroxy compound using a system obtained by reaction of $NaBH_4$ with (R,R)-tartaric acid, an ee of up to 78% being obtained. In contrast to this, the asymmetric reduction of propiophenone with the reaction product of $NaBH_4$ and (S,S)-tartaric acid afforded (S)-1-phenyl-1-propanol in an optical yield of only 10%.

EP-A1-0 320 096 likewize describes the reduction of prochiral keto esters or ketones by means of $NaBH_4$ and tartaric acid. In the examples, it is shown here that the use of (R,R)-tartaric acid yields the corresponding (R)-hydroxy compounds in an optical yield of only 15 to at most 85%.

In Synthetic Communications, 14(10), 955–959 (1984), the efficiency of the $NaBH_4$/tartaric acid system in the reduction of cyclic ketones was investigated. In the course of this, ketones, such as 2-methyl-, 3-methyl-, 4-methyl- and 4-t-butylcyclohexanone were reduced to the corresponding alcohols, markedly higher proportions of the more stable equatorial alcohols being obtained with the $NaBH_4$/tartaric acid system than with $NaBH_4$ alone. A change in the optical activity of the tartaric acid had no detectable effect on the stereochemical result of the reduction.

Rather, it can be derived from the literature that the stereoselectivity is strongly dependent on the structure of the substrate and that chiral centers present in the substrate, and/or the nature and size of the substituents of the substrate, have a strong influence on the course of the reduction. This is confirmed, for example, by J. Org. Chem. 1999, 64, 2172–2173. In this reference, the stereoselectivity in the reduction of β-hydroxy or β-alkoxy ketones by means of $SmI_2$ was investigated, it being found that it was possible to reduce substituents having the β-hydroxy substituent in high yield and good optical purity, the hydroxyl group to a significant extent determining both the stereoselectivity and the reaction rate. Substrates which had a protected β-hydroxyl group, for example a β-OBn or OTBS group, were almost completely inert in comparison with compounds having the free hydroxyl group. In the case of these substrates, no reduction was achieved. It also follows from J. Org. Chem., Vol. 56, No. 24, 1991 that the size of the substituents has a great influence on the stereoselectivity.

Unexpectedly, it has now been found that α- or β-ketoesters which have a chiral center in the γ position can be reduced with $NaBH_4$ and (D)- or (L)-tartaric acid to the corresponding diastereomeric hydroxy esters in each case in high optical purity and high yield, the chiral center present in the starting compound having no influence on the formation of the diastereomers.

The invention accordingly relates to a process for the stereoselective reduction of chiral α- or β-keto esters, which comprises reducing α- or β-ketoesters which have a chiral center in the γ position in an inert solvent at temperatures from −80 to +50° C. using a reductant obtained by reaction of $NaBH_4$ and (D)- or (L)-tartaric acid to the corresponding diastereomeric hydroxy compounds in each case.

Chiral α- or β-keto esters which have a chiral center in the γ position are reduced in the process according to the invention. Suitable substrates accordingly preferably have an open-chain, optionally branched alkyl or alkenyl chain. The alkyl or alkenyl chain consists here of 4 to 30, preferably 4 to 15, C atoms. In the case of an alkenyl chain, this can have 1 to 3 double bonds. The chain is substituted in position 1 by a carboxylate group. The ester group is derived here from a primary, secondary or tertiary alcohol. Esters of primary alcohols are preferred. These are accordingly $C_1$–$C_{20}$-, preferably $C_3$–$C_6$-, alkyl esters, such as methyl, ethyl, propyl, butyl, hexyl esters, etc. A keto group is found either in the α or β position to the carboxylate, preferably in the α position. The substrates have a chiral center in the γ position. A protected OH group, for example a t-butyldiphenylsilyloxy group, a trimethylsilyloxy group, a benzyloxy group or another customary protective group, is preferably found as a substituent in the γ position.

Particularly preferred substrates are those which can be prepared from unsaturated cyanohydrins by means of the Blaise reaction. Methyl (4S)-3-oxo-4-tert-butylsilyloxyundec-5-enoate is very particularly preferred.

According to the invention, the corresponding substrate is reduced using a reductant which is obtained by reaction of $NaBH_4$ with (D)- or (L)-tartaric acid.

Depending on which diastereomer of the corresponding hydroxy compound is desired, $NaBH_4$ is reacted here either with (D)- or with (L)-tartaric acid. The preparation of the actual reductant (the sodium acyloxyborohydride derived from (D)- or (L)-tartaric acid) is preferably carried out in situ, as described, for example, in Synthetic Communications, 14(10), 955–959 (1984); Bull. Chem. Soc. Jpn., 64, 175–182 (1991) or J. Chem. Soc. Perkin Trans I, 1827 (1990) etc. Preferably, the corresponding tartaric acid and $NaBH_4$ are suspended here in a suitable inert diluent which preferably also serves as a solvent for the reduction, $NaBH_4$ in turn preferably being added in portions to a solution of the tartaric acid and the suspension thus obtained being heated to reflux temperature for 0.5 to 6 hours. Suitable diluents or solvents are, for example, alcohols, such as, for example, 2-propanol, t-butanol, etc., ethers, such as tetrahydrofuran (THF), dioxane, diethyl ether etc., aromatics, such as benzene, toluene, xylene, etc. or other solvents which are inert under the reaction conditions. Optionally, the above solvents can also be employed as a solvent mixture. THF or 2-propanol is preferably employed. The molar ratio of $NaBH_4$ to (D)- or (L)-tartaric acid is between 1:0.5 to 1:1.5, the molar ratio preferably being 1:1.

Following the warming of the suspension, the mixture is cooled down to −50° C., preferably to −30° C. and particularly preferably to −20° C. A solution of the substrate to be reduced is then introduced into the solution of the reductant thus obtained. Suitable solvents are once again the solvents listed above. Preferably, the same solvent is employed in the in situ preparation of the reductant and in the reduction. Preferably, the substrate solution is added in a number of portions, particularly preferably dropwise, so that the temperature is kept constant at, particularly preferably, −20° C.

The reductant is present here in an excess relative to the substrate. A molar ratio of substrate to reductant of 1:2 to 1:6, particularly preferably of approximately 1:4, is preferred. The reaction mixture is stirred in the course of this. After reduction is complete, i.e. depending on the selected substrate after 1 to 60 hours, hydrochloric acid or sulfuric acid, for example, is added to the reaction mixture for the isolation of the corresponding diastereomer, or for the termination of the reaction. Preferably, ethyl acetate or other suitable solvents, and, if appropriate, sodium chloride are additionally added until the saturation point is reached. After phase separation has taken place, the final product is extracted from the organic phase and purified.

By means of the process according to the invention, it is unexpectedly possible by the selection of D- or L-tartaric acid to obtain the corresponding diastereomeric hydroxy compound in high yield and optical purity. In particular, this is particularly advantageous in the reduction of (4S)-methyl-3-oxo-4-tert-butylsilyloxyundec-5-enoate, since using the process according to the invention, depending on whether (D)- or (L)-tartaric acid is employed, either (3R, 4S)- or (3S, 4S)-methyl-3-hydroxy-4-tert-butylsilyloxyundec-5-enoate can specifically be prepared in excellent diastereomeric excess of over 90%. These compounds are valuable intermediates for the preparation of an inhibitor for protein kinase C or for L-AZT (azidothymidine), a potential anti-HIV agent. Accordingly, the invention further relates to the use of methyl (3R, 4S)- or (3S, 4S)-3-hydroxy-4-tertbutylsilyloxyundec-5-enoate prepared according to the invention for the preparation of the corresponding enantiomerically and diastereomerically pure lactones (4R, 5S)-5-hydroxymethyl-4-tetradecanoyltetrahydrofuran-2-one and (4S, 5S)-5-(E-hept-1-enyl)-4-hydroxytetrahydrofuran-2-one, and its further reaction to give the L-AZT intermediate (2R, 4S, 5S)-5-acetoxy-3-azido-2-hydroxymethyloxolane.

The further reaction of (3R, 4S)-methyl-3-hydroxy-4-tert-butylsiloxyundec-5-enoate to give (4R, 5S)-5-hydroxymethyl-4-tetradecanoyltetrahydrofuran-2-one, an inhibitor of protein kinase C, has a total yield of 32%, whereas previously known preparation variants, such as described, for example, in J. Am. Chem. Soc., 1992, 114, 1059–1070, lead to yields of only 8%. The further processing according to the invention additionally needs only 7 stages, whereas previously 14 stages were customary.

The use according to the invention of (3R, 4S)-methyl-3-hydroxy-4-tert-butylsilyloxyundec-5-enoate (A) for the preparation of (4R, 5S)-5-hydroxymethyl-4-tetradecanoyltetrahydrofuran-2-one (E) accordingly comprizes the following steps:

a) reaction with tetrabutylammonium fluoride (TBAF) in a solvent which is inert under the reaction conditions, such as, for example, THF, at 10 to 40° C., preferably at 20–30° C., and isolation of the intermediate (4R, 5S)-5-(E-hept-1-enyl)-4-hydroxytetrahydrofuran-2-one (C) by extraction, then b) reaction with a mixture of pyridine and myristoyl chloride in $CH_2Cl_2$ at 10 to 40° C., preferably at 20–30° C., and isolation of the intermediate (4R, 5S)-5-(E-hept-1-enyl)-4-tetradecanoyltetrahydrofuran-2-one (D) by extraction, and subsequently c) reaction with ozone at –80 to –60° C., heating to 10 to 40° C., preferably at 20–30° C. and isolation of the final product (4R, 5S)-5-hydroxymethyl-4-tetradecanoyltetrahydrofuran-2-one (E) by addition of $BH_3:Me_2S$ under a rare gas atmosphere, and also of MeOH after 10 to 30 h.

The intermediate compound for L-AZT is obtained by the following steps by the use according to the invention of methyl (3S, 4S)-3-hydroxy-4-tert-butylsilyloxyundec-5-enoate (B):

a) reaction with TBAF in a solvent which is inert under the reaction conditions, such as, for example, THF at 10 to 40° C., preferably at 20–30° C., and isolation of the intermediate (4S, 5S)-5-(E-hept-1-enyl)-4-hydroxytetrahydrofuran-2-one (F), then b) reaction with a cooled (0 to 10° C., preferably 5° C.) solution of imidazole in DMF and t-butyldiphenylsilyl chloride, warming to 10 to 40° C., preferably to 20–30° C., and isolation of the intermediate (4S,5S)-4-tert-butyldiphenylsiloxy-5-(E-hept-1-enyl)tetrahydrofuran-2-one (G) by extraction, additionally c) reaction with diisobutylaluminum hydride (DIBAL) under a rare gas atmosphere at –80 to –60° C., warming to 10 to 40° C., preferably to 20–30° C., and isolation of the intermediate (2S, 4S, 5S)-5-acetoxy-3-tert-butyldiphenylsilyloxy-2-(E-hept-1-enyl)oxolane (H) by extraction, additionally d) reaction of a cooled solution (0 to 10° C., preferably 5° C.) of (2S, 4S, 5S)-5-acetoxy-3-tert-butyldiphenylsilyloxy-2-(E-hept-1-enyl)oxolane with TBAF, warming to 10 to 40° C., preferably to 20–30° C., and isolation of the intermediate (2S, 4S, 5S)-5-acetoxy-2-(E-hept-1-enyl)-3-hydroxyoxolane (I) by extraction, and e) reaction of a cooled solution (0 to 10° C., preferably 5° C.) of (2S, 4S, 5S)-5-acetoxy-2-(E-hept-1-enyl)-3-hydroxyoxolane with pyridine and with trifluoroacetic anhydride, addition of sodium azide followed by DMF, warming to 10 to 40° C., preferably to 20–30° C., and isolation of the intermediate (2S, 4S, 5S)-5-acetoxy-3-azido-2-(E-hept-1-enyl)oxolane (J) by extraction and f) reaction with ozone, reduction analogously to Hoffman, J. Org. Chem. 1997 (62), 2458–2465 or Hudlicky, J. Org. Chem. 1998 (63)510–520 and isolation of the final product (2R, 4S, 5S)-5-acetoxy-3-azido-2hydroxymethyloxolane (K).

EXAMPLE 1

(3R,4S)-Methyl-3-hydroxy-4-tert-butylsilyloxyundec-5-enoate (A)

$NaBH_4$ (2.42 g, 64 mmol) was added in portions to a solution of D-tartaric acid (9.6 g, 64 mmol) in dry THF (150 ml), and the suspension thus obtained was heated at reflux temperature for 2.5 h and then cooled to –20° C. A solution of (4S)-methyl-3-oxo-4-tert-butylsilyloxyundec-5-enoate (7.54 g, 16 mmol) in dry THF (75 ml) was then added dropwise, the temperature remaining at –20° C. After 40 h, hydrochloric acid (1M, 150 ml) was added to the reaction mixture, on account of which the temperature increased to room temperature. The mixture was stirred for a further 15 minutes. Ethyl acetate (500 ml), followed by solid sodium chloride, was then introduced until the saturation point was reached. The aqueous phase was separated off and extracted with a further 200 ml of ethyl acetate. The organic phases were combined, washed twice with 150 ml in each case of saturated sodium bicarbonate solution and then with 100 ml of a saturated sodium chloride solution, dried over sodium sulfate, filtered and concentrated under reduced pressure. The crude product was purified by column chromatography (90:10 to 80:20), petroleum ether:ethyl acetate), by means of which methyl (3R, 4S)-3-hydroxy-4-tert-butylsilyloxyundec-5-enoate was obtained as a colorless oil in a yield of 93% (6.97 g, 14.7 mmol).

d.e.=92% (chiral HPLC, OD—H, 99.75:0.25 heptane:isopropanol, 0.6 ml/min. 254 nm); $^1$H NMR ($CDCl_3$, 200 MHz): δ (ppm) 0.88 (t, 3H), 1.07 (s, 9H), 1.13–1.30 (m, 3H), 1.74–1.84 (m, 2H), 2.44 (d, 1H, J=2.38 Hz), 2.47 (s, 1H), 2.62 (d, 1H, J=3.47 Hz), 3.67 (s, 3H), 4.01–4.12 (m, 2H), 5.14–5.44 (m, 2H), 7.30–7.49 (m, 6H), 7.62–7.73 (m, 4H), $^{13}$C NMR (CDCl$_3$, 200 MHz): δ (ppm), 14.06, 19.41, 22.51, 27.11, 28.45, 31.37, 32.14, 37.07, 51.76, 71.67, 77.61, 127.43, 127.69, 129.66, 129.84, 133.57, 133.81, 135.71, 135.95, 136.08, 172.59.

EXAMPLE 2

Methyl(3S,4S)-3-hydroxy-4-tert-butylsilyloxyundec-5-enoate (B)

NaBH$_4$ (2.03 g, 53.72 mmol) was added in portions to a solution of L-tartaric acid (8.06 g, 53.72 mmol) in dry THF (125 ml), and the suspension thus obtained was heated at reflux temperature for 2.75 h and then cooled to −20° C. A solution of methyl (4S)-3-oxo-4-tert-butylsilyloxyundec-5-enoate (5.38 g, 11.55 mmol) in dry THF (75 ml) was then added dropwise, the temperature remaining at −20° C. After 43 h, hydrochloric acid (1M, 125 ml) was added to the reaction mixture, on account of which the temperature increased to room temperature. The mixture was stirred for a further 15 minutes. Ethyl acetate (500 ml), followed by solid sodium chloride, was then introduced until the saturation point was reached. The aqueous phase was separated off and extracted with a further 200 ml of ethyl acetate. The organic phases were combined, washed twice with 150 ml in each case of saturated sodium bicarbonate solution and then with 100 ml of a saturated sodium chloride solution, dried over sodium sulfate, filtered and concentrated under reduced pressure. The crude product was purified by column chromatography (90:10 to 80:20), petroleum ether:ethyl acetate), by means of which methyl (3R, 4S)-3-hydroxy-4-tert-butylsilyloxyundec-5-enoate was obtained as a colorless oil in a yield of 89% (4.77 g, 10.20 mmol).

d.e.=92% (chiral HPLC, OD—H, 99.75:0.25 heptane:isopropanol, 0.6 ml/min., 254 nm); $^1$H NMR (CDCl$_3$, 200 MHz): δ (ppm) 0.88 (t, 3H), 1.07 (s, 9H), 1.13–1.30 (m, 3H), 1.77–1.86(m, 2H), 2.36 (dd, 1H, J=15.63, 8.60 Hz), 2.53 (dd, 1H, J=15.87, 3.23 Hz), 2.76 (d, 1H, J=3.85 Hz), 3.68 (s, 3H), 3.97–4.08 (m, 2H), 5.16–5.41 (m, 2H), 7.31–7.49 (m, 6H) 7.63–7.71 (m, 4H), $^{13}$C NMR (CDCl$_3$, 200 MHz): δ (ppm), 14.06, 19.43, 22.51, 27.11, 28.37, 31.37, 32.14, 37.39, 51.78, 71.74, 77.71, 127.43, 127.71, 129.67, 129.85, 133.51, 133.70, 135.81, 135.92, 136.07, 172.66

EXAMPLE 3

Preparation of (4R, 5S)-5-hydroxymethyl-4-tetradecanoyltetrahydrofuran-2-one (E) from methyl (3R, 4S)-3-hydroxy-4-tert-butylsilyloxyundec-5-enoate (A)

a) 0.691 M TBAF in 30.0 ml of acetonitrile (20.74 mmol) was added dropwise to a cooled (5° C.) solution of A (6.47 g, 13.83 mmol), prepared analogously to Example 1, in 165 ml of THF. After 48 hours at room temperature, 300 ml of ethyl acetate were added and the organic phase was washed with brine (3×25 ml), dried, filtered and concentrated in vacuo. The residue was purified by means of column chromatography (70:30 to 50:50, petroleum ether:ethyl acetate). Yield of (4R, 5S)-5-(E-hept-1-enyl)-4-hydroxytetrahydrofuran-2-one (C) as a white solid: 85% (2.23 g, 11.8 mmol).

$^1$H NMR (CDCl$_3$, 200 MHz): δ (ppm) 0.86 (t, 3H, J=7.08 Hz), 1.21–1.43 (m, 6H), 2.04 (q, 2H, J=6.84 and 6.54), 2.47 (dd, 1H, J=17.82 and 3.66 Hz), 2.78 (dd, 1H, J=17.77 and 6.16 Hz), 3.12 (bs, 1H), 4.30 (m, 1H), 4.79 (dd, 1H, J=6.34 and 2.44 Hz), 5.42 (dd, 1H, J=15.38 and 6.57 Hz), 5.83 (dt, 1H, J=15.38 and 7.56 Hz) ; $^{13}$C NMR (CDCl$_3$, 200 MHz): δ (ppm), 14.04, 22.48, 28.43, 31.34, 32.23, 37.02, 72.21, 87.98, 124.34, 136.34, 172.59.

b) A mixture of 90 mg of pyridine (1.13 mmol) and 224 mg of myristoyl chloride (0.90 mmol) in 2 ml of CH$_2$Cl$_2$ was added with stirring to a solution of C (150 mg; 0.75 mmol) in 1 ml of CH$_2$Cl$_2$. The solution thus obtained was stirred at room temperature for a further 20 h. A mixture of CH$_2$Cl$_2$/H$_2$O (15 m each) was then added and the organic phase was washed with H$_2$O (2×10 ml), CuSO$_4$ (3% w/v; 10 ml) and brine (10 ml). The organic phase was separated off, dried, filtered and concentrated in vacuo. The residue was purified by means of column chromatography (95:05, petroleum ether:ethyl acetate). Yield of (4R, 5S)-5-(E-hept-1-enyl)-4-tetradecanoyltetrahydrofuran-2-one (D) as a white solid: 85% (249 mg, 0.51 mmol).

$^1$H NMR (CDCl$_3$, 200 MHz); δ (ppm) 0.86 (t, 3H, J=7.08 Hz), 1.18–1.45 (m and overlapping s, 26H), 1.53–1.70 (m, 2H), 2.04 (q, 2H, J=7.82 and 6.10), 2.33 (t, 2H, J=7.33 Hz), 2.52 (dd, 1H, J=18.31 and 1.76 Hz), 2.90 (dd, 1H, J=18.31 and 6.54 Hz), 4.91 (d, 1H, J=5.56 Hz), 5.12 (dt, 1H, J=6.40 and 1.71 Hz), 5.46 (ddt, 1H, J=15.52, 5.70 and 1.33 Hz), 5.83 (dt, 1H, J=15.44 and 6.72 Hz); $^{13}$C NMR (CDCl$_3$, 200 MHz): δ (ppm), 14.04, 14.17, 22.49, 22.74, 28.39, 29.10, 29.26, 29.40, 29.47, 29.63, 29.68, 31.33, 31.96, 32.18, 33.74, 34.12, 73.62, 84.76, 123.67, 135.98, 172.97, 174.13.

c) Ozone was passed through a solution of 75 mg of D (0.18 mmol) in 9 ml of CH$_2$Cl$_2$ at −78° C. for one hour. The solution was then warmed to room temperature, stirred for 15 minutes and then treated under an argon atmosphere with BH$_3$:Me$_2$S (1M in CH$_2$Cl$_2$; 0.75 ml; 0.75 mmol) dropwise in the course of 25 minutes. After 20 h, 0.5 ml of MeOH was added and the mixture was stirred for a further 2 h. The reaction mixture was concentrated in vacuo and the residue was purified by means of column chromatography (90:10 to 65:35, petroleum ether:ethyl acetate). Yield of (4R, 5S)-5-hydroxymethyl-4-tetradecanoyltetrahydrofuran-2-one (E) as a white solid: 40% (25 mg, 0.07 mmol).

$^1$H NMR (CDCl$_3$, 200 MHz): δ (ppm) 0.88 (t, 3H, J=7.08 Hz), 1.23 (s, 20H), 1.55=1.68 (m, 2H), 2.33 (t, 2H, J=7.32 Hz), 2.55 (dd, 1H, J=18.58 and 1.90 Hz), 3.07 (dd, 1H, J=18.60 and 7.54 Hz), 3.93 (m, 2H), 4.50 (m, 1H), 5.36 (dt, 1H, J=7.43 and 1.71 Hz); $^{13}$C NMR (CDCl$_3$, 300 MHz): δ (ppm), 14.36, 22.94, 24.98, 29.32, 29.46, 29.59, 29.67, 29.88, 32.17, 34.32, 35.68, 62.54, 71.75, 85.73, 173.74, 175.38

EXAMPLE 4

Preparation of (2R,4S,5S)-5-acetoxy-3-azido-2-hydroxymethyloxolane (K) from (3S, 4S)-methyl-3-hydroxy-4-tert-butylsilyloxyundec-5-enoate (B)

a) 0.691 M TBAF in 21.6 ml of acetonitrile (20.74 mmol) was added dropwise to a cooled (5° C.) solution of B (4.67 g, 9.97 mmol), prepared analogously to Example 2, in 118 ml of THF. After 20 hours at room temperature, 300 ml of ethyl acetate were added and the organic phase was washed with brine (3×25 ml), dried, filtered and concentrated in vacuo. The residue was purified by means of column chromatography (60:40 to 40:60, petroleum ether:ethyl acetate). Yield of (4S, 5S)-5-(E-hept-1-enyl)-4-hydroxytetrahydrofuran-2-one (F) as a white solid: 90% (1.78 g, 8.98 mmol).

¹H NMR (CDCl₃, 200 MHz): δ (ppm) 0.88 (t, 3H, J=7.08 Hz), 1.23–1.53 (m, 6H), 2.04 (q, 2H, J=6.83 and 6.73), 2.27 (bs, 1H), 2.59 (dd, 1H, J=17.63 and 1.41 Hz), 2.78 (dd, 1H, J=17.57 and 5.12 Hz), 4.46 (m, 1H), 4.86 (dd, 1H, J=6.84 and 3.18 Hz), 5.58 (dd, 1H, J=15.49 and 6.89 Hz), 5.97 (dt, 1H, J=15.49 and 6.73 Hz); ¹³C NMR (CDCl₃, 200 MHz): δ (ppm), 14.06, 22.51, 28.48, 31.39, 32.49, 38.77, 69.77, 84.88, 121.35, 139.03, 175.58.

b) 2.49 g of tert-butyldiphenylsilyl chloride (9.09 mmol) were added to a cooled solution (5° C.) of 825 mg of imidazole (12.12 mmol) in DMF (0.5 ml). After 15 minutes, the compound F (1.20 g; 6.06 mmol) was added dropwise, and the reaction mixture was warmed to room temperature and stirred at this temperature for 4 h. 100 ml of water were then added and the aqueous phase was extracted with CH₂Cl₂ (3×75 ml). The organic extracts were combined, dried, filtered and concentrated in vacuo. The residue was purified by means of column chromatography (90:10 to 85:15, petroleum ether:ethyl acetate). Yield of (4S, 5S)-4-tert-butyldiphenylsilyloxy-5-(E-hept-1-enyl) tetrahydrofuran-2-one (G) as a colorless liquid: 77% (2.04 g, 4.67 mmol).

¹H NMR (CDCl₃, 200 MHz): δ (ppm) 0.90 (t, 3H, J=6.51 Hz), 1.08 (s, 9H), 1.22–1.46 (m, 6H), 2.07–2.16 (m, 2H), 2.29–2.51 (m, 2H), 4.5–4.54 (m, 1H), 4.67–4.72 (m, 1H), 5.82–5.86 (m, 2H), 7.34–7.49 (m, 6H), 7.59–7.65 (m, 4H); ¹³C NMR (CDCl₃, 200 MHz): δ (ppm), 14.08, 19.27, 22.58, 26.85, 28.41, 31.50, 32.48, 38.88, 71.63, 85.63, 123.39, 127.85, 127.98, 130.12, 130.22, 132.58, 133.08, 135.78, 135.89, 138.11, 175.25.

c) The solution of G was treated with DIBAL (1M in hexane; 11.6 ml; 11.6 mmol) in the course of 15 minutes at −78° C. and under an argon atmosphere. After 1.5 h, 2 ml of water were added and the reaction mixture was stirred at −78° C. for a further 15 minutes before it warmed to room temperature, at which it was stirred for a further 1.5 h. The mixture was diluted with 100 ml of Et₂O, poured into a saturated solution of sodium ditartrate (110 ml) and stirring was continued. After 1 h, the aqueous phase was extracted with Et₂O (3×100 ml), and the organic extracts were combined, dried, filtered and concentrated in vacuo. The residue was dissolved in 30 ml of CH₂Cl₂, cooled to 5° C. and treated with a solution of acetic anhydride (2.46 ml; 26.13 mmol) and 4-dimethylaminopyridine (DMAP) (47 mg; 0.387 mmol). The mixture was stirred for 3.5 h, in the course of which it warmed to room temperature. The mixture was then poured into a saturated NaHCO₃ solution (40 ml). The aqueous phase was extracted with Et₂O (4×40 ml), and the organic extracts were combined, dried, filtered and concentrated in vacuo. The residue was purified by means of column chromatography (90:10 to 85:15, petroleum ether:ethyl acetate). Yield of (2S, 4S, 5S)-5-acetoxy-3-tert-butyldiphenylsilyloxy-2-(E-hept-1-enyl)oxolane (H) as a colorless oil: 66% (1.22 g; 2.54 mmol).

¹H NMR (CDCl₃, 200 MHz): δ (ppm) 0.89 (t, 3H, J=6.59 Hz), 1.07 (s, 9H), 1.25–1.49 (m, 6H), 1.88–2.24 (m and overlapping s, 7H ), 4.37–4.43 (m, 1H), 4.45–4.52 (m, 1H), 5.74–5.77 (m, 2H), 6.37 (dd, 2H, 7.34–7.49 (m, 6H), 7.59–7.65 (m, 4H); ¹³C NMR (CDCl₃, 200 MHz): δ (ppm) 14.07, 19.28, 21.31, 26.90, 28.56, 31.58, 32.51, 42.33, 74.04, 84.54, 97.66, 125.30, 127.76, 127.67, 129.82, 129.89, 133.27, 133.92, 135.84, 135.96, 136.41, 170.36.

d) TBAF (1M in THF; 0.30 ml; 0.30 mmol) was added dropwise in the course of 10 minutes to a cooled (5° C.) solution of H (140 mg, 0.296 mmol) in 4 ml of THF. After stirring at room temperature for 1.5 hours, the reaction mixture was poured into ethyl acetate/water (10 ml/5 ml) and the aqueous phase was extracted with ethyl acetate (2×10 ml). The organic phases were combined, washed, dried, filtered and concentrated in vacuo. The residue was purified by means of column chromatography (80:20 to 75:25, petroleum ether:ethyl acetate). Yield of (2S, 4S, 5S)-5-acetoxy-2-(E-hept-1-enyl)-3-hydroxyoxolane (I) as a colorless oil: 60% (42 mg, 0.174 mmol).

¹H NMR (CDCl₃, 200 MHz): δ (ppm) 0.85 (t, 3H, J=6.59 Hz), 1.22–1.50 (m, 6H), 1.81 (bs, 1H), 2.00–2.14 (m and overlapping s, 5H), 2.35 (ddq, 2H, J=12.51, 5.86 and 2.19 Hz), 4.30–4.36 (m, 1H), 4.55 (dd, 1H, J=6.35 and 2.69 Hz), 5.51 (ddt, 1H, J=15.63, 6.60 and 1.41 Hz), 5.91 (dt, 1H, J=15.57 and 6.59 Hz), 6.42 (dd, 1H, J=5.86 and 2.25 Hz); ¹³C NMR (CDCl₃, 200 MHz): δ (ppm), 14.03, 21.32, 22.51, 28.64, 31.43, 32.54, 41.98, 72.42, 83.62, 97.64, 122.93, 137.43, 170.38.

e) 42 mg of pyridine (0.53 mmol), followed by 74 mg of trifluoroacetic anhydride (0.352 mmol), were added in one portion and with stirring to a cooled solution (5° C.) of 42 mg of the compound I (0.176 mmol) in 0.5 ml of CH₂Cl₂. After stirring for a further 45 minutes, 114 mg of sodium azide (1.76 mmol), followed by 1 ml of DMF, were added, in the course of which the reaction mixture warmed to room temperature, at which it was stirred further overnight. After addition of 10 ml of CH₂Cl₂, the organic phase was washed with water (3×5 ml), dried, filtered and concentrated in vacuo. The residue was purified by means of column chromatography (90:10 to 70:30, petroleum ether:ethyl acetate). Yield of (2S, 4S, 5S)-5-acetoxy-3-azido-2-(E-hept-1-enyl) oxolane (J) as a colorless oil: 49% (24 mg; 0.085 mmol) and 24% (10 mg; 0.041 mmol) of recovered starting compound I.

¹H NMR (CDCl₃, 200 MHz): δ (ppm) 0.88 (t, 3H, J 6.59 Hz), 1.22–1.45 (m, 6H), 1.98–2.20 (m and overlapping s, 6H), 2.60 (ddd, 1H, J=14.54, 8.60 and 5.62 Hz), 3.73 (dt, 1H, J=10.55, 8.79 and 5.13 Hz), 4.47 (t, 1H, J=6.59 Hz), 5.40 (ddt, 1H, J=15.30, 7.33 and 1.28 Hz), 5.91 (dt, 1H, J=15.38 and 6.64 Hz), 6.31 (dd, 1H, J=5.67 and 1.81 Hz); ¹³C NMR (CDCl₃, 200 MHz): δ (ppm), 14.06, 21.32, 22.52, 28.45, 31.36, 32.26, 37.71, 63.64, 84.75, 97.06, 126.12, 136.80, 170.29.

f) The final compound (2R, 4S, 5S)-5-acetoxy-3-azido-2-hydroxymethyloxolane (K) was prepared from J by reaction with ozone and reduction analogously to Hoffman, J. Org. Chem. 1997 (62), 2458–2465 or Hudlicky, J. Org. Chem 1998 (63) 510–520.

What is claimed is:

1. A process for the stereoselective reduction, of chiral α- or β-keto esters, which comprises reducing α- or β-keto esters which have a chiral center in the γ position in an inert solvent at temperatures from −80 to +50° C. using a reductant obtained by reaction of NaBH₄ and (D)- or (L)-tartaric acid to give the corresponding diastereomeric hydroxy compounds in each case.

2. The process as claimed in claim 1, wherein, as substrate, a compound having an open chain, optionally branched alkyl or alkenyl chain having 4 to 30 C atoms is employed, the alkenyl chain having 1 to 3 double bonds, which open or branched chain is substituted in position 1 by a carboxylate group having 1 to 20 C atoms in the ester moiety and has a keto group in the α or β position relative to the carboxylate group and a chiral center in the γ-position.

3. The process as claimed in claim 1, wherein, as substrate, methyl (4S)-3-oxo-4-tert-butylsilyloxyundec-5-enoate is employed.

4. The process as claimed in claim 1, wherein the reductant is prepared in situ by reaction of $NaBH_4$ and (D)- or (L)-tartaric acid.

5. The process as claimed in claim 1, wherein the solvent employed is 2-propanol, t-butanol, tetrahydrofuran, dioxane, diethyl ether, benzene, toluene or xylene or a mixture thereof.

6. The process as claimed in claim 3, wherein methyl (4S)-3-oxo-4-tert-butylsilyloxyundec-5-enoate is reduced, depending on the tartaric acid employed, to (3R, 4S) or methyl (3S, 4S)-3-hydroxy-4-tertbutylsilyloxyundec-5-enoate in an optical purity of over 90% d.e.

7. Method for the preparation of (E, 2S, 4S, 5S)-2-0-acetyl-4-azido-5-hydroxymethyldihydrofuran which comprises reacting methyl (3R, 4s)- or (3S, 4S)-3-hydroxy-4-tert-butylsilyloxyundec-5-enoate to form the corresponding enantiomerically and diastereomerically pure lactones (4R, 5S)-5-hydroxymethyl-4-tetradecanoyltetrahydrofuran-2-one or (4S, 5S)-5-(E-hept-1-enyl)-4-hydroxytetrahydrofuran-2-one, and further reacting it to form (E, 2S, 4S, 5S)-2-acetyl-4-azido-5-hydroxymethyldihydrofuran.

8. Method for the preparation of (4R, 5S)-5-hydroxymethyl-4-tetradecanoyltetrahydrofuran-2-one, which comprises
   a) reacting methyl (3R, 4S)-3-hydroxy-4-tertbutylsilyloxyundec-5-enoate with tetrabutylammonium fluoride in a solvent which is inert under the reaction conditions at 10 to 40° C. and isolating the intermediate (4R, 5S)-5-(E-hept-1-enyl)-4-hydroxytetrahydrofuran-2-one by extraction,
   b) reacting the intermediate from a) with a mixture of pyridine and myristoyl chloride in $CH_2Cl_2$ at 10 to 40° C. and isolating of the intermediate (4R, 5S)-5-(E-hept-1-enyl)-4-tetradecanoyltetrahydrofuran-2-one by extraction, and then
   c) reacting the intermediate from b) with ozone at –80 to –60° C., warming to 10 to 40° C. and isolating the final product (4R, 5S)-5-hydroxymethyl-4-tetradecanoyltetrahydrofuran-2-one by adding $BH_3{:}Me_2S$ under a rare gas atmosphere, and then adding MeOH after 10 to 30 hours.

9. Method for the preparation of (2R, 4S, 5S)-5-acetoxy-3-azido-2-hydroxymethyloxolane, which comprises
   a) reacting methyl (3S, 4S)-3-hydroxy-4-tertbutylsilyloxyundec-5-enoate with TBAF in a solvent which is inert under the reaction conditions at 10 to 40° C. and isolating the intermediate (4S, 5S)-5-(E-hept-1-enyl)-4-hydroxytetrahydrofuran-2-one,
   b) reacting the intermediate from a) with a cooled solution of imidazole in DMF and t-butyldiphenylsilylchloride, warming to 10 to 40° C. and isolating the intermediate (4S, 5S)-4-tertbutyldiphenylsilyloxy-5-(E-hept-1-enyl)tetrahydrofuran-2-one by extraction,
   c) reacting the intermediate from b) with diisobutylaluminum hydride under a rare gas atmosphere at –80 to –60° C., warming to 10 to 40° C. and isolating the intermediate (2S, 4S, 5S)-5-acetoxy-3-tertbutyldiphenylsilyloxy-2-(E-hept-1-enyl)oxolane by extraction,
   d) reacting a cooled solution of (2S, 4S, 5S,)-5-acetoxy-3-tert-butyldiphenylsilyloxy-2-(E-hept-1-enyl)oxolane with TBAF, warming to 10 to 40° C. and isolating the intermediate (2S, 4S, 5S)-5-acetoxy-2-(E-hept-1-enyl)-3-hydroxyoxolane by extraction,
   e) reacting a cooled solution of (2S, 4S, 5S)-5-acetoxy-2-(E-hept-1-enyl)-3-hydroxyoxolane with pyridine and with trifluoroacetic anhydride, adding sodium azide, followed by DMF, warming to 10 to 40° C. and isolating the intermediate (2S, 4S, 5S)-5-acetoxy-3-azido-2-(E-hept-1-enyl) oxolane by extraction and
   f) reacting the intermediate from e) with ozone, subsequently reducing and isolating the final product (2R, 4S, 5S)-5-acetoxy-3-azido-2-hydroxymethyloxolane.

* * * * *